(12) United States Patent
Thomas et al.

(10) Patent No.: US 9,764,133 B2
(45) Date of Patent: Sep. 19, 2017

(54) PORTABLE TENS APPARATUS AND METHOD OF USE THEREOF

(71) Applicant: Modular Therapeutx, LLC, Soddy Daisy, TN (US)

(72) Inventors: Charles M. Thomas, Hixson, TN (US); D. Keith Hagy, Hixson, TN (US); Donald Kay Riker, Soddy Daisy, TN (US); Nathan Anderson Pollock, Suffolk Park (AU); Brad Peter Ryan, Clinton (AU); Lee Anthony Rodezno, Rowville (AU); Troy Christiaan Nyssen, Jannali (AU)

(73) Assignee: Modular Therapeutx, LLC, Soddy Daisy, TN (US)

( * ) Notice: Subject to any disclaimer, the term of this patent is extended or adjusted under 35 U.S.C. 154(b) by 68 days.

(21) Appl. No.: 14/599,077

(22) Filed: Jan. 16, 2015

(65) Prior Publication Data

US 2015/0174402 A1    Jun. 25, 2015

Related U.S. Application Data

(63) Continuation-in-part of application No. 13/738,610, filed on Jan. 10, 2013, now Pat. No. 8,972,016.

(Continued)

(51) Int. Cl.
*A61N 1/00* (2006.01)
*A61N 1/36* (2006.01)
(Continued)

(52) U.S. Cl.
CPC ..... *A61N 1/36021* (2013.01); *A61N 1/36014* (2013.01); *A61N 1/025* (2013.01);
(Continued)

(58) Field of Classification Search
CPC .. A61N 1/025; A61N 1/0456; A61N 1/36014; A61N 1/36021; A61N 1/0472–1/0496
See application file for complete search history.

(56) References Cited

U.S. PATENT DOCUMENTS

| | | |
|---|---|---|
| 4,442,839 A | 4/1984 | Maurer et al. |
| 4,453,548 A | 6/1984 | Maurer et al. |

(Continued)

FOREIGN PATENT DOCUMENTS

| | | |
|---|---|---|
| WO | WO 99/64105 A1 | 12/1999 |
| WO | WO 2005/002668 A1 | 1/2005 |

OTHER PUBLICATIONS

International Search Report and Written Opinion of International Searching Authority for Corresponding PCT Application.

(Continued)

*Primary Examiner* — Lindsey G Wehrheim
(74) *Attorney, Agent, or Firm* — Chambliss, Bahner & Stophel, P.C.

(57) ABSTRACT

A TENS apparatus includes a portable TENS device having a housing with a lower surface and a pair of integral electrodes that are incorporated into the lower surface of the housing. The portable TENS device includes a pulse driver that is located within the housing and adapted to generate a program of pulse waveforms for TENS therapy without a carrier wave, and a wireless transceiver component that is operatively connected to the pulse driver. The TENS apparatus includes a remote controller that is provided for communicating with the wireless transceiver component of the portable TENS device by means of a wireless communication signal in order to allow for wireless activation and control of the pulse driver of the portable TENS device.

11 Claims, 8 Drawing Sheets

Related U.S. Application Data

(60) Provisional application No. 61/631,916, filed on Jan. 13, 2012.

(51) Int. Cl.
*A61N 1/04* (2006.01)
*A61N 1/02* (2006.01)

(52) U.S. Cl.
CPC .......... *A61N 1/0456* (2013.01); *A61N 1/0472* (2013.01); *A61N 1/0496* (2013.01)

(56) References Cited

U.S. PATENT DOCUMENTS

| | | |
|---|---|---|
| 4,723,552 A | 2/1988 | Kenyon et al. |
| 4,769,881 A | 9/1988 | Pedigo et al. |
| 4,887,603 A | 12/1989 | Morawetz et al. |
| 4,918,745 A * | 4/1990 | Hutchison .......... A61N 1/36032 379/52 |
| 4,922,908 A | 5/1990 | Morawetz et al. |
| 5,048,523 A | 9/1991 | Yamasawa et al. |
| 5,052,391 A | 10/1991 | Silberstone et al. |
| 5,423,874 A * | 6/1995 | D'Alerta ............ A61N 1/36021 607/46 |
| 5,991,655 A | 11/1999 | Gross et al. |
| 6,023,642 A | 2/2000 | Shealy et al. |
| 6,445,955 B1 * | 9/2002 | Michelson ......... A61N 1/36003 607/2 |
| 2002/0068961 A1 | 6/2002 | Fischer et al. |
| 2002/0193844 A1 | 12/2002 | Michelson et al. |
| 2005/0107831 A1 | 5/2005 | Hill et al. |
| 2007/0123952 A1 | 5/2007 | Strother et al. |
| 2007/0276449 A1 | 11/2007 | Gunter et al. |
| 2009/0132018 A1 * | 5/2009 | DiUbaldi ............. A61N 1/0456 607/152 |
| 2010/0004715 A1 | 1/2010 | Fahey |
| 2010/0023098 A1 | 1/2010 | Li et al. |
| 2010/0114238 A1 * | 5/2010 | Muccio ................ A61N 1/0452 607/46 |
| 2010/0217349 A1 | 8/2010 | Fahey |
| 2010/0274327 A1 | 10/2010 | Carroll et al. |
| 2011/0224753 A1 | 9/2011 | Palermo et al. |
| 2011/0276112 A1 | 11/2011 | Simon et al. |
| 2012/0330384 A1 * | 12/2012 | Perryman ......... A61N 1/36125 607/72 |

OTHER PUBLICATIONS

Ruskin, "Charge it:DCs are using electrotherapy products such as TENS, interferential, and combo units to help patients . . . ," Chiropractic Products, 22(10), p. 22(2), Oct. 2007.

Ward et al., "Comparison of the Hypoalgesic Efficacy of Low-Frequency and Burst-Modulated Kilohertz Frequency Currents," Physical Therapy, 87(8), pp. 1056-1063, Aug. 2007.

* cited by examiner

PORTABLE TENS APPARATUS AND METHOD OF USE THEREOF

CROSS-REFERENCE TO RELATED APPLICATION

This application is a continuation-in-part of U.S. patent application Ser. No. 13/738,610, which was filed on Jan. 10, 2013, now U.S. Pat. No. 8,972,016, and which claims the benefit of U.S. Provisional Patent Application No. 61/631,916, filed on Jan. 13, 2012.

FIELD OF THE INVENTION

The present invention relates generally to a transcutaneous electrical nerve stimulation (TENS) device that generates neuromuscular electrical stimulation in the form of a unique asymmetrical biphasic square pulse. More particularly, the invention relates to a portable TENS device that employs integral electrodes for electric current dispersion across the surface of the user's skin which device may be wirelessly controlled by a remote controller.

BACKGROUND OF THE INVENTION

Pain is the mental manifestation of a neurological response to various physiological and psychological ailments. Sometimes pain corresponds to or serves as a warning of physical damage or biological dysfunction. Sometimes pain is a characteristic of a biological transition. In any event, control and alleviation of pain has been an important function of medicine for as long as medical practitioners have existed. The most common pain-control methods employ bio-active chemical agents that act to block neurotransmission pathways within the body. However, sometimes such chemical agents are ineffective or produce unacceptable side effects. Consequently, neuromuscular electrical stimulation (NMES) has also been employed to alleviate pain.

Two types of NMES that can be used to alleviate pain are burst-modulated alternating current ("BMAC") and pulsed current ("PC"). BMAC is commonly applied by use of interferntial current or "Russian current" stimulators, whereas PC is commonly applied by a transcutaneous electrical nerve stimulation ("TENS") device. In the application of BMAC, two medium-frequency (i.e., 1 KHz-100 KHz) carrier waves are caused to interfere with each other, resulting in an interference current frequency that is equal to the difference between the interfering frequencies. For example, if current A is at 4000 Hz and current B is at 3900 Hz, their interaction would produce an interference current having a beat frequency of 100 Hz that is carried on a 3950 Hz frequency carrier wave. The advantage to BMAC is that it can be used to apply electrical stimulation to much deeper tissues than PC. A TENS device never employs a carrier wave, and it produces PC electrical stimulation at much lower frequencies (i.e., typically within the range of 2-150 Hz) than are employed in the application of BMAC. PC electrical stimulation is thought to work by blocking pain impulses from the brain, whereas BMAC can heal damaged tissues.

TENS is generally employed for the alleviation of pain by application to muscles through electrodes that are attached to or placed upon the surface of the skin. Most commonly, a TENS unit is attached to one or more pairs of electrodes by wires, and these electrodes are adhesively attached to the skin of the patient. A therapist controls the operation of the device to achieve the desired results.

Notes on Construction

The use of the terms "a", "an", "the" and similar terms in the context of describing the invention are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. The terms "substantially", "generally" and other words of degree are relative modifiers intended to indicate permissible variation from the characteristic so modified. The use of such terms in describing a physical or functional characteristic of the invention is not intended to limit such characteristic to the absolute value which the term modifies, but rather to provide an approximation of the value of such physical or functional characteristic. All methods described herein can be performed in any suitable order unless otherwise specified herein or clearly indicated by context.

The use of any and all examples or exemplary language (e.g., "such as") herein is intended merely to better illuminate the invention and not to place a limitation on the scope of the claimed invention. Nothing in the specification should be construed as indicating any element as essential to the practice of the invention unless so stated with specificity.

As used herein, the term "lower", when used to describe a relative location on or with respect to a portable TENS device having integral electrodes that is used to apply NMES through the skin of a user, refers to a direction or location adjacent to or nearer to the skin of the user when the device is in use.

SUMMARY OF THE INVENTION

The invention comprises a method and apparatus for therapeutic use in for the reduction of chronic and acute pain. The apparatus includes a compact, portable TENS device having integral electrodes that may be placed on the skin of a user and a remote controller. The portable TENS device includes a housing having a lower surface and a pair of integral electrodes that are incorporated into the lower surface of the housing. The portable TENS device also includes a pulse driver that is located within the housing and adapted to generate a program of pulse waveforms for TENS therapy without a carrier wave, and a wireless transceiver component that is operatively connected to the pulse driver. The remote controller is adapted to communicate with the wireless transceiver component of the portable TENS device by means of a wireless communication signal that allows for wireless activation and control of the pulse driver of the portable TENS device.

Preferably, the portable TENS device generates an asymmetrical biphasic square pulse waveform that is applied in a program that incorporates both accepted theories of electrical stimulation for pain management into a single consolidated protocol. This preferred program utilizes the Opiate Release Theory for long term analgesia and the Gate Control Theory for immediate pain relief of short duration. This preferred program provides for enhanced user comfort that encourages compliance with the treatment regimen.

In order to facilitate an understanding of the invention, the preferred embodiment of the invention is illustrated in the drawings, and a detailed description thereof follows. It is not intended, however, that the invention be limited to the particular embodiment described or to use in connection with the apparatus illustrated herein. Various modifications and alternative embodiments such as would ordinarily occur to one skilled in the art to which the invention relates are also contemplated and included within the scope of the invention described and claimed herein.

BRIEF DESCRIPTION OF THE DRAWINGS

The presently preferred embodiments of the invention are illustrated in the accompanying drawing drawings, in which.

DESCRIPTION OF THE PREFERRED EMBODIMENT OF THE INVENTION

Figure 1:
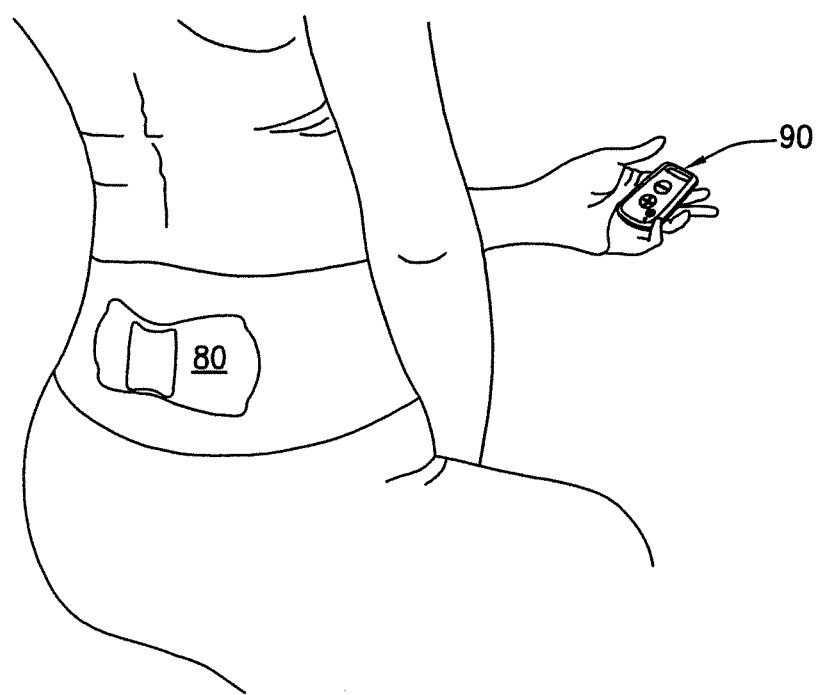
FIG. 1 illustrates the use of a preferred embodiment of the apparatus by a patient.
Figure 2:
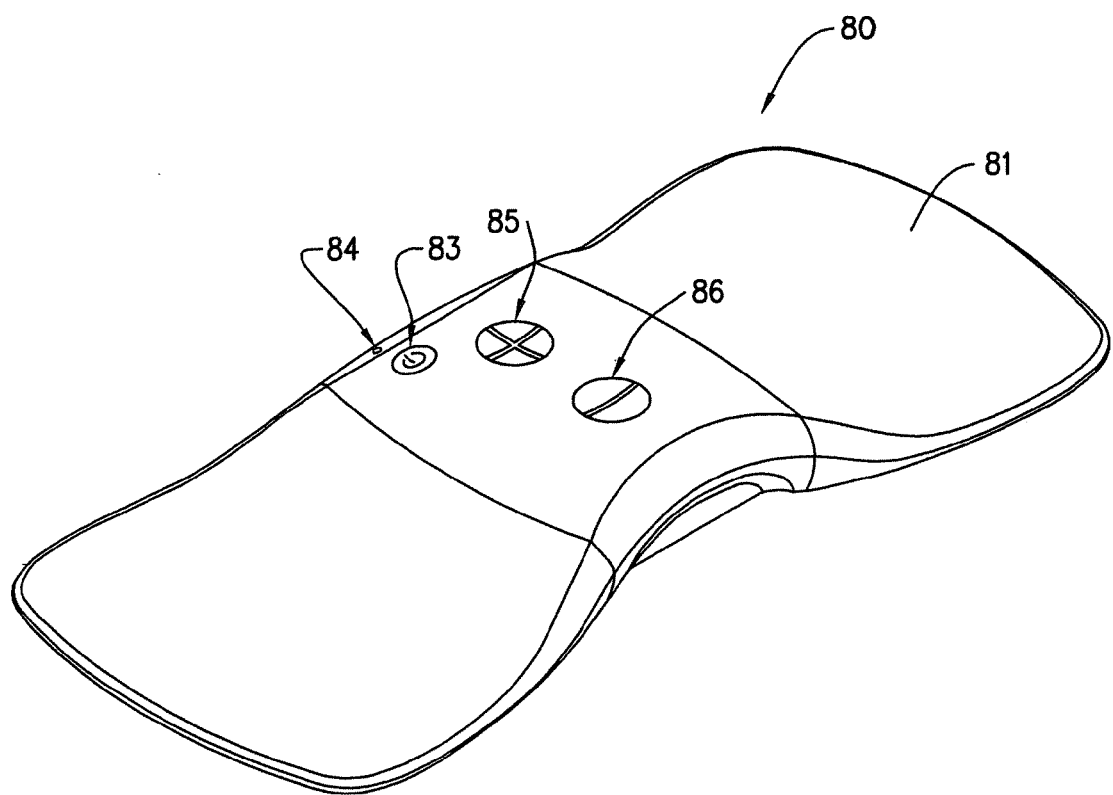
FIG. 2 is a top perspective view of a preferred embodiment of the portable TENS device.
Figure 3:
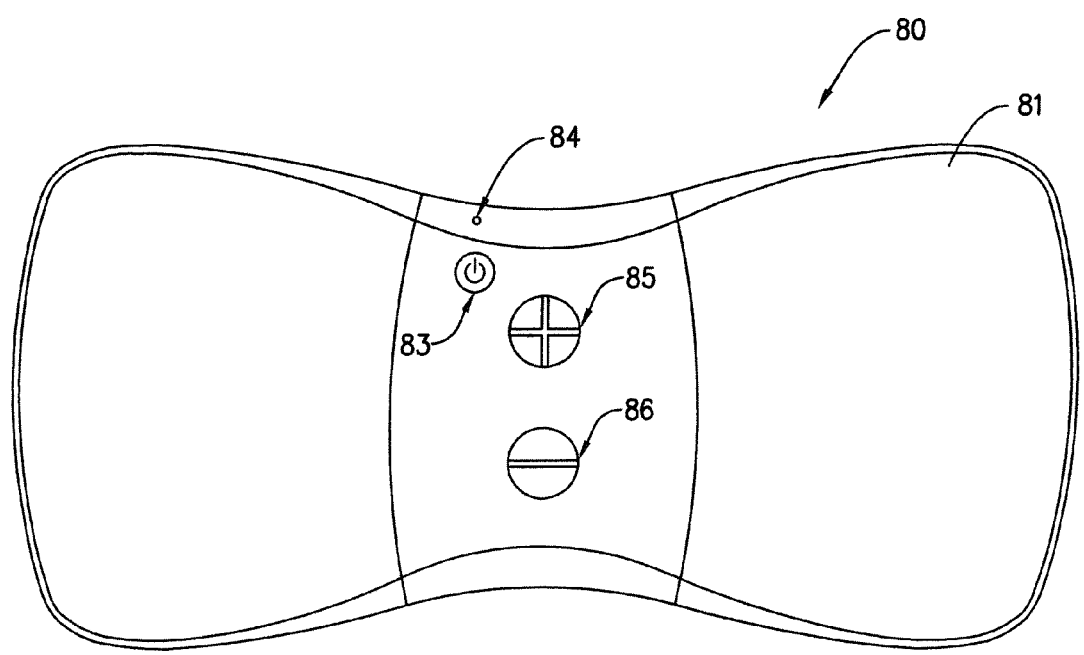
FIG. 3 is a top view of the embodiment of the portable TENS device shown in FIGS. 1 and 2.
Figure 4:
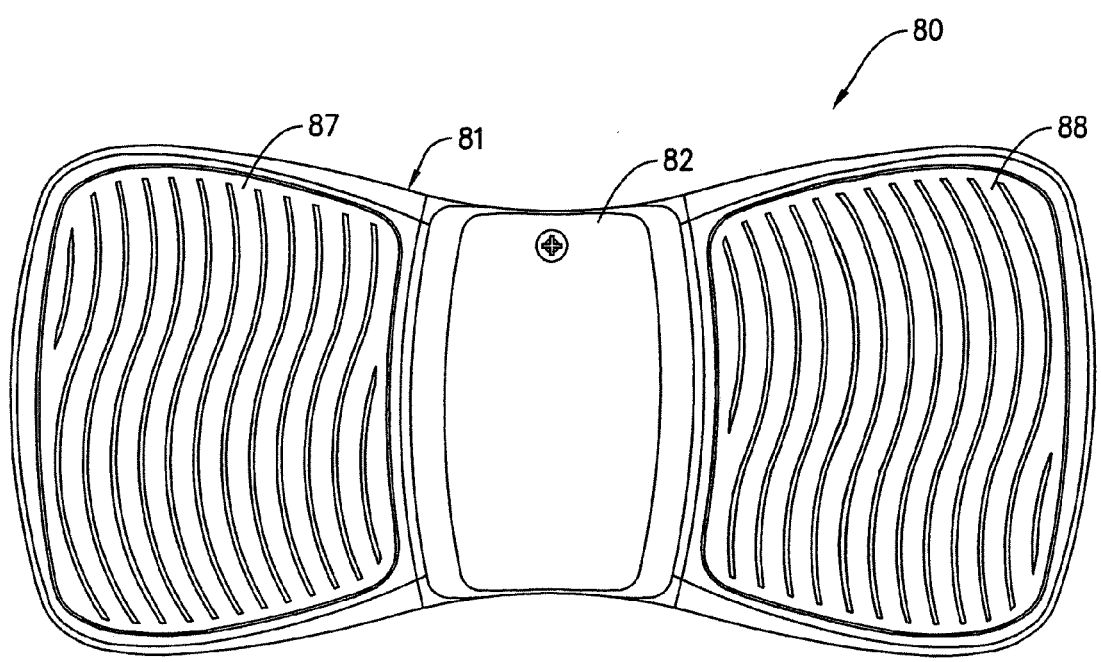
FIG. 4 is a bottom view of the embodiment of the portable TENS device illustrated in FIGS. 1-3, showing the integral electrodes.

FIG. 1 shows a preferred embodiment 80 of the portable TENS device comprising housing 81 that has been placed into contact with the skin of the patient in the lower lumbar region. Of course, the efficacy of the device is not limited to placement in the lower lumbar region, or even to placement on the user's back. The device may be placed in other locations on the body suitable for TENS therapy. The preferred embodiment of the device is powered by one or more replaceable batteries located under access plate 82 (see FIG. 4) of housing 81. In the alternative, the portable TENS device may be powered by one or more rechargeable batteries. As shown in FIGS. 2-4, TENS device 80 includes on-off button 83 which controls switch 17 (see FIG. 7) for activating and de-activating device 80. Device 80 also includes indicator light 84, and optional increase and decrease buttons 85 and 86 respectively, for controlling the intensity of the electrical current applied, on its top side, and a pair of integral electrodes 87 and 88 which are incorporated into the lower surface of housing 81.

Figure 5:
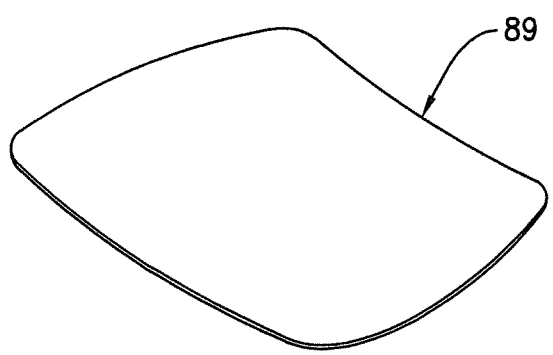
FIG. 5 is a perspective view of a preferred embodiment of a gel pad for use in connection with the embodiment of the portable TENS device shown in FIGS. 1-4.

Preferably, the device is adhesively attached to the skin of a user with a pair of removable and replaceable conductive hydrogel pads 89. As can be seen by comparing FIGS. 4 and 5, these pads are preferably sized and shaped to conform to the size and shape of electrodes 87 and 88, and are adapted to be placed between electrodes 87 and 88 and the skin of a user to provide electric current dispersion across a relatively large surface of the skin. Preferably, housing is relatively compact so that the area of the portion of the lower surface of housing 81 that is occupied by electrodes 87 and 88 is at least about 50% of the total area of the lower surface, and most preferably at least about 70% of the total area of the lower surface of housing 81.

Upon attachment of the device to the skin, the user may activate the device using on-off button 83 and may control the intensity of the electrical current applied using buttons 85 and 86. In the alternative, device 80 may be activated and controlled by remote controller 90 (best shown in FIG. 6). The remote controller electronically pairs with device 80 through a wireless communication signal that allows for wireless activation and control of the TENS device. The signal may be a radio signal, or it may employ a Bluetooth®, mobile or cell phone application or any other type of wireless communications signal. Remote controller 90 comprises housing 91 and includes on-off button 92, which controls switch 60 (see FIG. 9) for activating and de-activating device 80. Remote controller 90 also includes indicator light 93 and increase and decrease buttons 94 and 95 respectively for controlling the intensity of the electrical current applied. The preferred embodiment of the wireless remote controller is also powered by one or more replaceable batteries, although an alternative embodiment may be powered by one or more rechargeable batteries.

Figure 7:
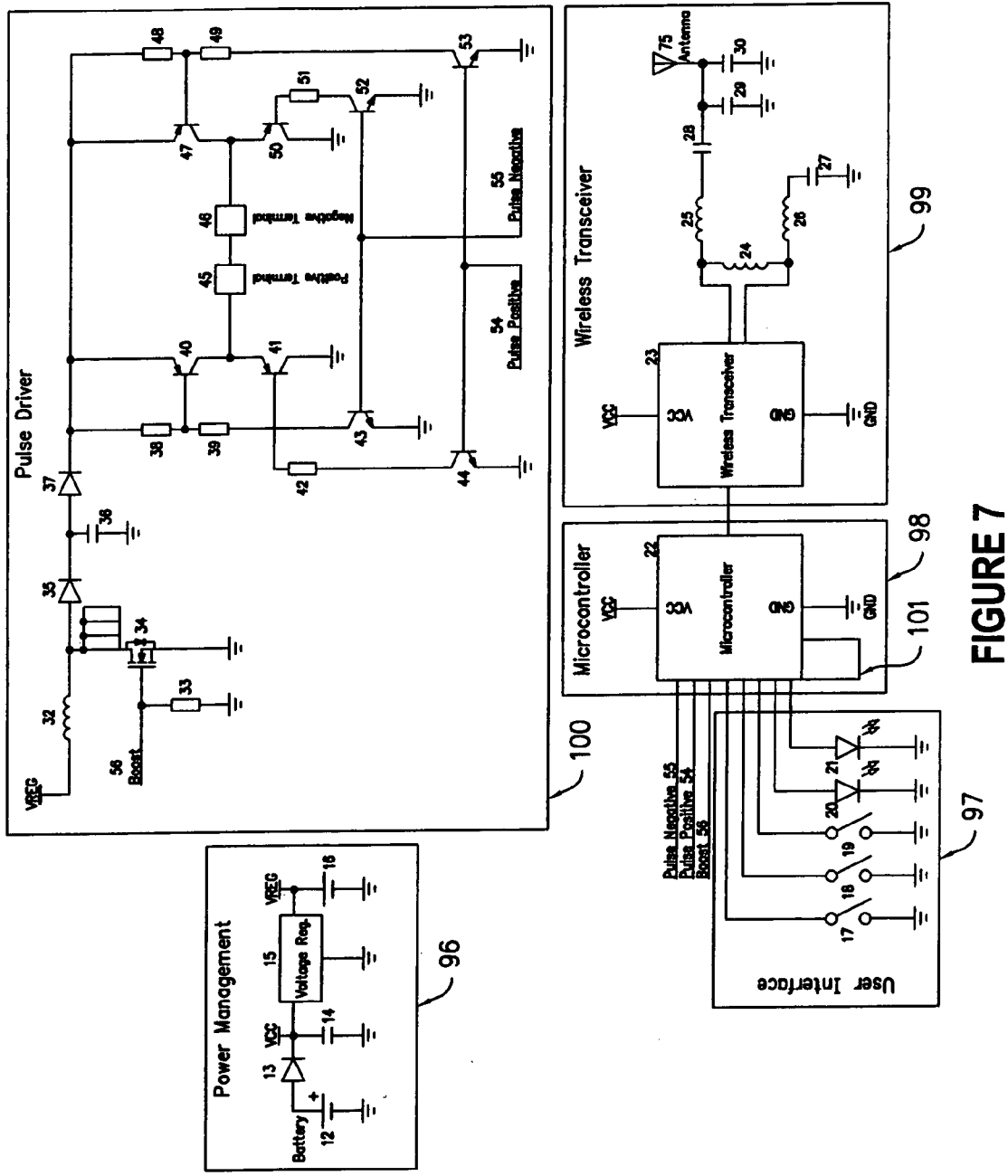
FIG. 7 is a circuit diagram for the preferred embodiment of the portable TENS device.

As shown in FIG. 7, preferred TENS device 80 includes five components that are contained within housing 81: a power management component that is illustrated schematically at 96, a user interface component that is illustrated schematically at 97, a microcontroller component that is illustrated schematically at 98, a wireless transceiver component that is illustrated schematically at 99 and a pulse driver that is illustrated schematically at 100.

Power management component 96 includes battery 12 and provides power to the other components of TENS device 80. Power management component 96 includes diode 13 for reverse polarity protection, and capacitor 14 for power supply decoupling. The output from the combination of battery 12, diode 13 and capacitor 14 (labeled VCC in FIG. 7) provides supply voltage to the microcontroller component 98 and to voltage regulator 15 of power management component 96. The output of voltage regulator 15 (labeled VREG in FIG. 7), buffered by capacitor 16, is then used as a regulated voltage supply for pulse driver component 100. Microcontroller component 98 contains the software which controls the various functions of preferred TENS device 80, including wireless communications, the operation of pulse driver 100 and the operation of user interface component 97. Microcontroller 22 of microcontroller component 98 is operatively connected to user interface component 97, to wireless transceiver component 99 and to pulse drive component 100. User interface component 97 provides user interaction with TENS device 80, including feedback from device 80 to the user. The user interface component comprises buttons 83, 85 and 86, and indicator light 84, which preferably is coupled to a pair of light emitting diodes ("LED")s 20 and 21. When the user interface buttons are pressed, microcontroller 22 of microcontroller component 98 provides feedback to the user by illuminating the LEDs. Microcontroller 22 interprets the pressing of on-off button 83, corresponding to user interface switch 17, as a request to start the TENS device program mode (if device 80 is in standby mode), or to stop the program mode if the device is operating.

Microcontroller 22 also interprets the pressing of button 85, which controls user interface switch 18, as a request to increase the intensity of the electrical output pulses. In the same manner, microcontroller 22 interprets the pressing of button 86, which controls user interface switch 19, as a request to decrease the intensity of the electrical output pulses.

In a preferred embodiment of the invention, indicator light 84 includes green LED 20 and yellow-orange LED 21. The green LED is illuminated in response to actions associated with normal operation, such as: (a) indicating that any of buttons 83, 85 and 86 have been pressed, (b) indicating that TENS device 80 is in standby mode, and (c) indicating that pairing of TENS device 80 with remote controller 90 has been achieved. In this embodiment of the invention, the yellow-orange LED is illuminated to indicate that the battery is in need of recharging or replacement.

Pulse driver 100 delivers electrical signals to the user through electrodes 87 and 88, as controlled by microcontroller 22. BOOST control line 56 is used to control the generation of the desired pulse voltage. In order to achieve this, a switching boost circuit is formed with inductor 32, resistor 33, MOSFET 34 and diode 35. Resistor 33 of the switching boost circuit insures that MOSFET 34 remains off, even if the output of microcontroller 22 should go to a high impedance state. Consequently, the only way that MOSFET 34 will turn on is if the microcontroller drives the voltage high across the switching boost circuit. By switching MOSFET 34 on and off in rapid succession through the BOOST control line 56, a higher voltage is built up across storage capacitor 36. The number of pulses on BOOST control line 56 is controlled by microcontroller 22 to insure that this voltage corresponds to the desired pulse intensity set by the user (using buttons 85 and 86 on TENS device 80 or buttons 94 and 95 on remote controller 90). Once the appropriate voltage has been built up, microcontroller 22 releases the voltage as a pulse to the user through pulse positive control line 54 and pulse negative control line 55. These pulses will appear as a voltage difference across the two output terminals 45 and 46 that are connected to electrodes 87 and 88.

Diode 37 serves as a reverse blocking diode, so that the pulse delivery circuit 38, 39, 40, 41, 42, 43, 44, 45, 46, 47, 48, 49, 50, 51, 52 and 53 will deliver a positive output pulse when pulse positive control line 54 is driven to a logical high voltage by microcontroller 22, while keeping pulse negative control line 55 at a logical low voltage. By reversing these logical levels (i.e. driving the pulse negative control line 55 to a logical high voltage while keeping the pulse positive control line 54 at a logical low voltage), a reverse polarity pulse will be delivered.

In one embodiment of the invention, microcontroller component 98 includes an analog-to-digital converter ("ADC") 101 (shown in phantom in FIG. 7). In this embodiment, the inputs of the ADC would be connected to one or more points in the pulse driver circuit, such as the positive terminal of capacitor 36, one or both of the output terminals 45 and 46, a terminal of battery 12 and/or the cathode of diode 37. In this embodiment of the invention, microcontroller 22 would use the ADC to determine the voltage at each point to which the ADC is connected in order to modify its control of the BOOST control line 56 to improve power efficiency in the operation of TENS device 80. This could allow the pulse driver power supply VREG to be connected directly to VCC 14, eliminating the need for voltage regulator 15. In such an embodiment, microcontroller 22 would modify the number of pulses used on BOOST line 56 in order to deliver a controlled output pulse voltage regardless of the supply voltage of the pulse driver circuit. The embodiment of the invention utilizing an ADC would also allow microcontroller 22 to determine the quality of the connection of electrodes 87 and 88 to the user (e.g. connection impedance) through comparison of the voltages before and after a pulse has been delivered. This information could be used to provide feedback to a user to assist in improving use of the TENS device. In addition, this information could be used to allow for an automatic shutdown of TENS device 80 if the user removes the device from contact with his/her body.

Figure 8:
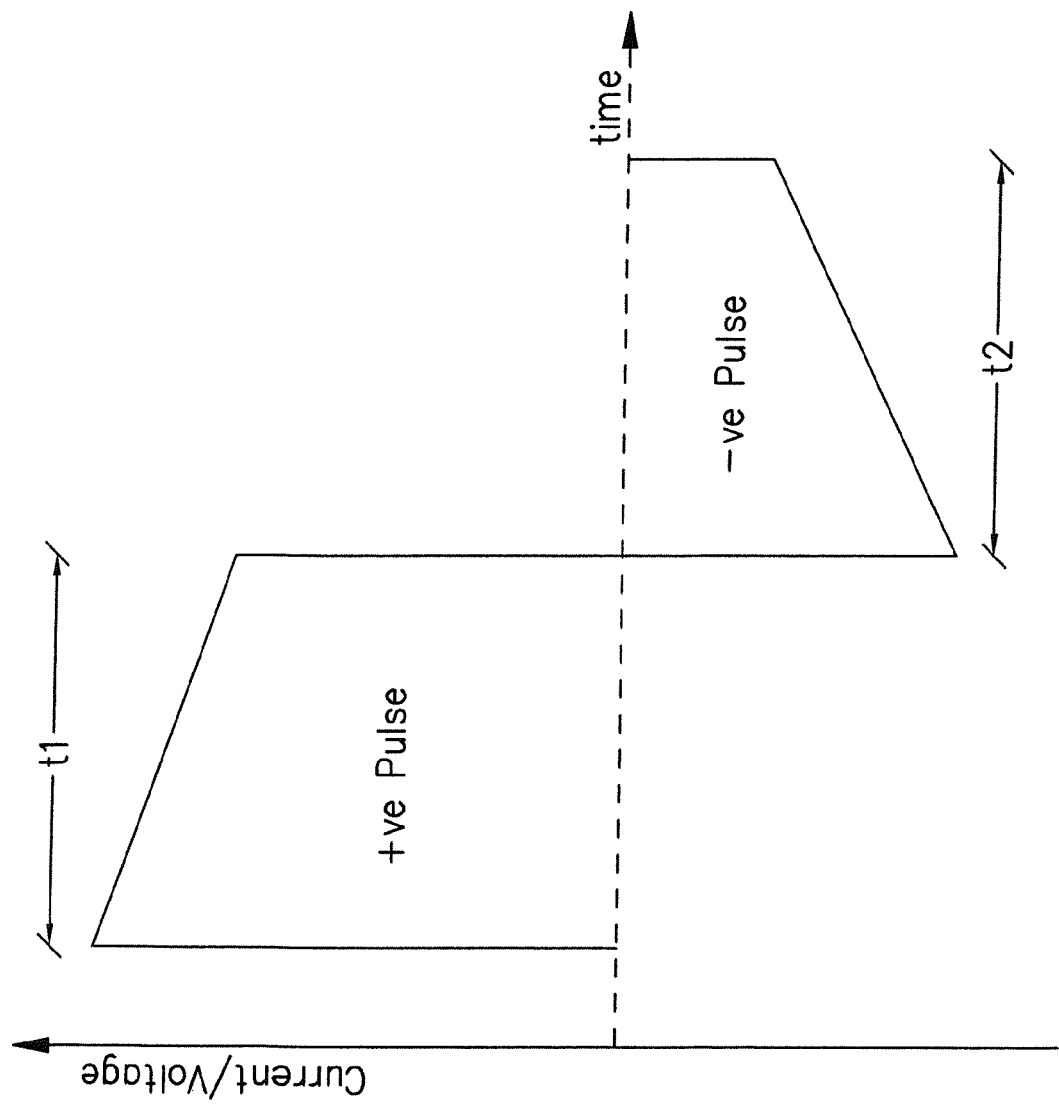
FIG. 8 illustrates the pulse waveform that is delivered by the preferred embodiment of the portable TENS device.

As shown in FIG. 8, the pulse waveform delivered by preferred TENS device 80 is an asymmetrical biphasic square waveform. This waveform is characterized by a positive pulse (identified as +ve Pulse in FIG. 8) followed by a negative pulse that is of a different shape (identified as −ve Pulse). The peak of the positive pulse is used as the reference of the peak output of the waveform. The duration or period of the pulse, shown as t1 for the positive pulse and t2 for the negative pulse, is known as the pulse width. In the preferred embodiment of the invention illustrated in FIG. 8, t1=t2. Upon activation, the preferred treatment program will automatically proceed through three stages, over a total period of thirty minutes, forty-two seconds, as summarized in the following table:

|  | Stage 1 | S1->S2 | Stage 2 | S2->S3 | Stage 3 | S3->end |
|---|---|---|---|---|---|---|
| Time | 5 minutes | 14 seconds | 20 minutes | 13 seconds | 5 minutes | 15 seconds |
| Cycle | Modulated | Freq Ramp Down | Modulated | Freq Ramp Up | Modulated | Freq Ramp Down |
| Frequency Modulation Range (up and down) | 80 Hz-120 Hz | 110 down to 5 Hz | 5 Hz-10 Hz | 5 up to 80 Hz | 80 Hz-120 Hz | 110 down to 0 Hz |
| Center Frequency | 100 Hz | N/A | 7.5 Hz | N/A | 100 Hz | N/A |
| Modulation Frequency | 20 Hz | N/A | 2.5 Hz | N/A | 20 Hz | N/A |
| Frequency Modulation (Time (from − to +) | 16 seconds | N/A | 5 seconds | N/A | 16 seconds | N/A |
| Frequency Change Interval | 1 second | N/A | 1 second | N/A | 1 second | N/A |
| Pulse Width | 120 μsec | 120 μsec | 240 μsec | 240 μsec | 120 μsec | 120 μsec |

This preferred treatment program provides five minutes of gate-control theory electrical current therapy for pain relief (stage one), followed by twenty minutes of opiate release theory electrical current therapy for pain relief (stage two) and another five minutes of gate-control theory electrical current therapy for pain relief (stage three). More particularly, in stage one, the preferred waveform is applied for a total of five minutes of pulsed modulated frequencies ranging between 80 Hz and 120 Hz. The frequency modulation time is sixteen seconds and the frequency change interval is one second. The pulse width in stage one is 120 μsec. The frequency of the waveform ramps up over a period of sixteen seconds from 80 Hz to 120 Hz, and then ramps down over a period of sixteen seconds from 120 Hz to 80 Hz. This ramp-up and ramp-down sequence is repeated over a total period of five minutes, with the ending frequency being 110 Hz. This first stage is followed by a fourteen second frequency ramp-down to 5 Hz, with the pulse width remaining at 120 μsec.

In the second stage of the program, TENS device 80 automatically applies the preferred waveform for a total of twenty minutes of pulsed modulated frequencies ranging between 5 Hz and 10 Hz. The frequency modulation time is five seconds and the frequency change interval is one second. The pulse width in step two is 240 μsec. The frequency of the waveform ramps up over a period of 5 seconds from 5 Hz to 10 Hz and then ramps down over a period of 5 seconds from 10 Hz to 5 Hz. This ramp-up and ramp-down sequence is repeated over a total period of 20 minutes, with the ending frequency being 5 Hz. This second stage is followed by a thirteen second frequency ramp-up to 80 Hz, with the pulse width remaining at 240 μsec.

In the third stage of the program, TENS device 80 automatically applies a waveform for a total of five minutes of pulsed modulated frequencies ranging between 80 Hz and 120 Hz. The frequency modulation time is 16 seconds and the frequency change interval is one second. The pulse width in stage three is 120 μsec. The frequency of the waveform ramps up over a period of 16 seconds from 80 Hz to 120 Hz, and then ramps down over a period of 16 seconds from 120 Hz to 80 Hz. This ramp-up and ramp-down sequence continues over a total period of five minutes, with the ending frequency being 110 Hz. This third stage is followed by a fifteen second ramp-down to 0 Hz, with the pulse width remaining at 120 μsec.

Microcontroller 22 of TENS device 80 can also receive user requests sent by remote controller 90. These requests are received by wireless transceiver component 99 of portable TENS device 80 through antenna 75. The antenna itself is attached to the wireless transceiver 23 of wireless transceiver component 99 through an impedance matching circuit 24, 25, 26, 27, 28, 29 and 30.

Figure 6:
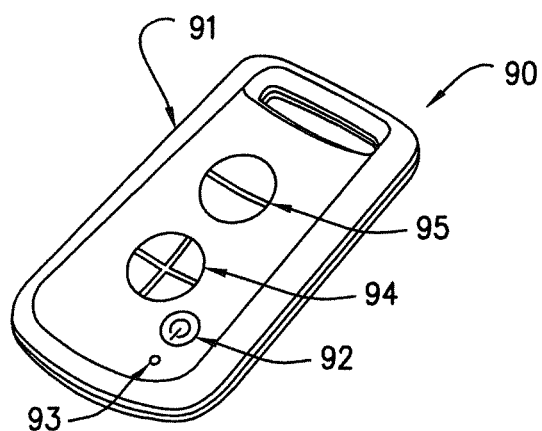
FIG. 6 is a top perspective view of a preferred embodiment of a remote controller for use in connection with the portable TENS device.

As shown in FIG. 6, remote controller 90 comprises housing 91, on-off button 92, indicator light 93, and intensity control buttons 94 and 95. Microcontroller 22 of microcontroller component 98 of preferred TENS device 80 interprets the signal obtained from the pressing of on-off button 92 of remote controller 90 as a request to start the TENS device program mode (if device 80 is in standby mode), or to stop the program mode if the device is operating. Microcontroller 22 also interprets the signal obtained by the pressing of button 94 of remote controller 90 as a request to increase the intensity of the electrical output pulses, and it interprets the signal obtained by the pressing of button 95 of remote controller 90 as a request to decrease the intensity of the electrical output pulses.

Figure 9:
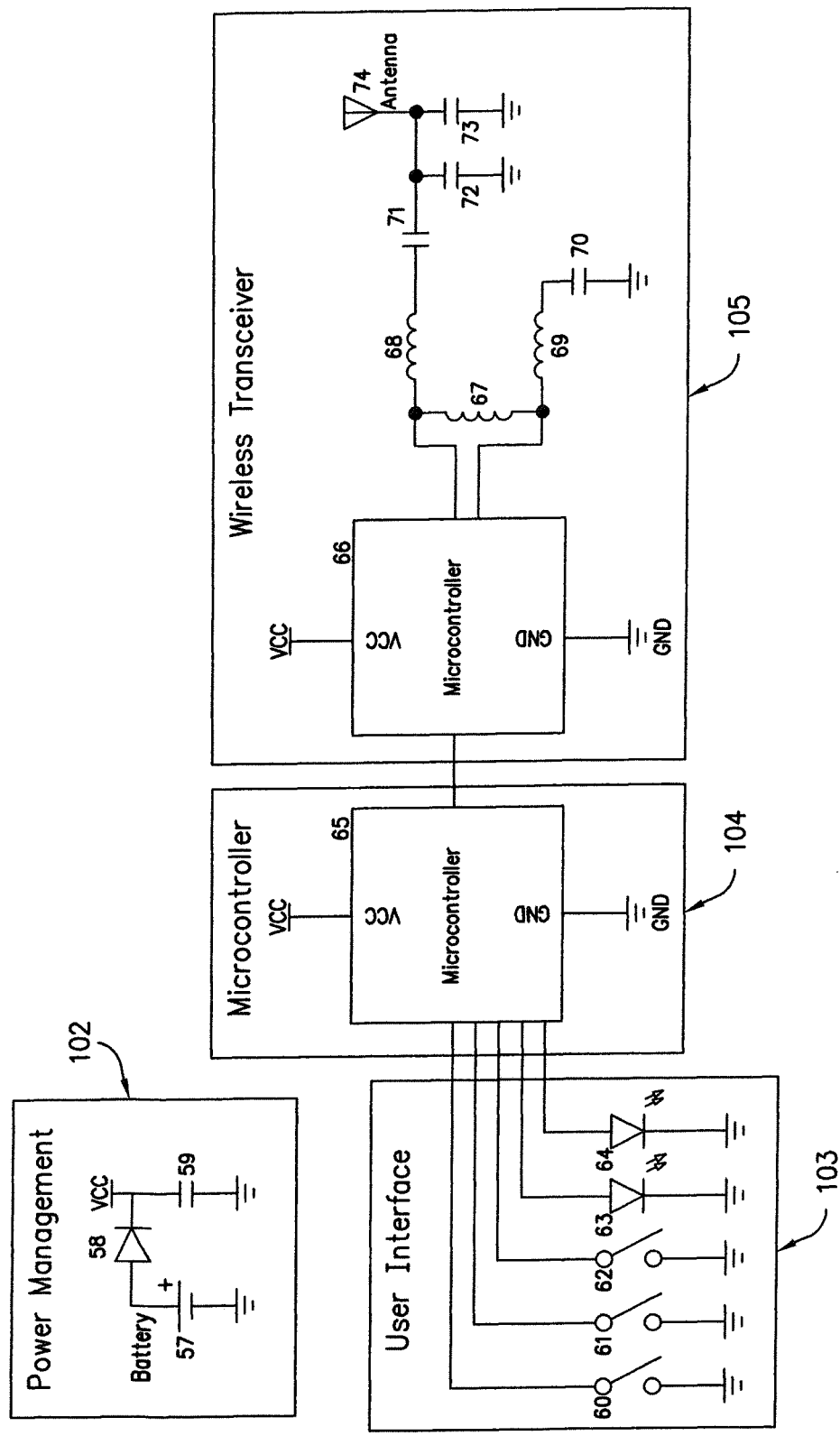
FIG. 9 is a circuit diagram for the preferred embodiment of the remote controller.

As shown in FIG. 9, preferred remote controller 90 includes four components that are contained within housing 91: a power management component that is illustrated schematically at 102, a user interface component that is illustrated schematically at 103, a microcontroller component that is illustrated schematically at 104 and a wireless transceiver component that is illustrated schematically at 105. Power management component 102 includes battery 57, diode 58 for reverse polarity protection, and capacitor 59 for power supply decoupling. The output power management component 102 (labeled VCC in FIG. 9) provides supply voltage to the remaining components of remote controller 90.

Microcontroller component 104 includes microcontroller 65, which contains the software which controls the various functions of preferred remote controller 90, including wireless communications and the operation of user interface 103. Microcontroller 65 of microcontroller component 104 is connected to user interface component 103 and to wireless transceiver component 105. User interface component 103 provides user interaction with remote controller 90, including feedback from remote controller 90 to the user. The user interface comprises buttons 92, 94 and 95, and indicator light 93, which preferably is coupled to a pair of LEDs 63 and 64. When the user interface buttons are pressed, microcontroller 65 of microcontroller component 104 provides feedback to the user by illuminating the LEDs. Microcontroller 65 interprets the pressing of on-off button 92, corresponding to user interface switch 60, as a request for wireless transceiver 66 to send a signal to TENS device 80 by means of impedance matching circuit 67, 68, 69, 70, 71, 72 and 73, and antenna 74 of wireless transceiver component 105 to start the program mode (if device 80 is in standby mode), or to stop the program mode if TENS device 80 is operating.

Microcontroller 65 also interprets the pressing of button 94, which controls user interface switch 61, as a request for wireless transceiver 66 to send a signal to TENS device 80 to increase the intensity of the electrical output pulses delivered by TENS device 80. In the same manner, microcontroller 65 interprets the pressing of button 95, which controls user interface switch 62, as a request for wireless transceiver 66 to send a signal to TENS device 80 to decrease the intensity of the electrical output pulses.

In a preferred embodiment of the invention, indicator light 93 includes green LED 63 and yellow-orange LED 64. The green LED is illuminated in response to actions associated with normal operation, such as: (a) indicating that any of buttons 92, 94 and 95 have been pressed, and (b) indicating that pairing of TENS device 80 with remote controller 90 has been achieved. In this embodiment of the invention, the yellow-orange LED is illuminated to indicate other than normal operation, such as: (a) that the wireless connection with TENS device 80 has been lost, or (b) that battery 57 is in need of recharging or replacement.

Although this description contains many specifics, these should not be construed as limiting the scope of the invention but as merely providing illustrations of the presently preferred embodiments thereof, as well as the best mode contemplated by the inventor of carrying out the invention. The invention, as described herein, is susceptible to various modifications and adaptations, as would be understood by those having ordinary skill in the art to which the invention relates.

What is claimed is:

1. A TENS apparatus comprising:
   (a) a portable TENS device which includes:
      (i) a housing having a lower surface;
      (ii) a pair of integral electrodes that are incorporated into the lower surface of the housing so that the area of the lower surface of the housing of the portable TENS device that is occupied by the integral electrodes is at least about 50% of the total area of the lower surface of the housing;
      (iii) a pulse driver that is located within the housing and adapted to generate a program of pulse waveforms for TENS therapy without a carrier wave;
      (iv) a wireless transceiver component that is operatively connected to the pulse driver;
   (b) a remote controller that is adapted to communicate with the wireless transceiver component of the portable TENS device by means of a wireless communication signal that allows for wireless activation and control of the pulse driver of the portable TENS device.

2. The TENS apparatus of claim 1 which includes a pair of removable and replaceable conductive hydrogel pads that are sized and shaped to conform to the size and shape of the integral electrodes, said hydrogel pads being adapted to adhesively attach the portable TENS device to the skin of a user.

3. The TENS apparatus of claim 2 wherein the pair of removable and replaceable conductive hydrogel pads are adapted to:
(a) maintain electrical contact between the integral electrodes and the skin of the user; and
(b) provide sufficient adhesive attachment to hold the portable TENS device in place on the skin of the user while the portable TENS device is in use.

4. The TENS apparatus of claim 1 wherein the portable TENS device includes a user interface component for providing feedback about the operation of the portable TENS device to a user.

5. The TENS apparatus of claim 1 wherein the portable TENS device includes:
(a) a power management component for providing power to the pulse driver;
(b) a microcontroller component for controlling the operation of the pulse driver.

6. The TENS apparatus of claim 5 wherein the microcontroller component of the portable TENS device includes an analog-to-digital converter that is adapted and configured to improve power efficiency in the operation of the TENS device.

7. The TENS apparatus of claim 5 wherein the microcontroller component of the portable TENS device includes an analog-to-digital converter that is adapted and configured to allow for an automatic shutdown of the portable TENS device if the user removes the device from contact with his/her body.

8. The TENS apparatus of claim 1 wherein the area of the lower surface of the housing of the portable TENS device that is occupied by the integral electrodes is at least about 70% of the total area of the lower surface of the housing.

9. A TENS apparatus comprising:
(a) a portable TENS device which includes:
(i) a housing having a lower surface;
(ii) a pair of integral electrodes that are incorporated into the lower surface of the housing;
(iii) a pulse driver that is located within the housing and adapted to generate a program of pulse waveforms for TENS therapy without a carrier wave, said program being adapted to alleviate pain without inducing a muscle contraction, wherein each of the pulse waveforms comprises an asymmetrical biphasic square waveform and where the program comprises a first stage period of gate-control theory electrical current therapy for pain relief in a first stage, followed by a second stage period of opiate release theory electrical current therapy for pain relief in a second stage and a third stage period of gate-control theory electrical current therapy for pain relief in a third stage;
(iv) a wireless transceiver component that is operatively connected to the pulse driver;
(b) a remote controller that is adapted to communicate with the wireless transceiver component of the portable TENS device by means of a wireless communication signal that allows for wireless activation and control of the pulse driver of the portable TENS device.

10. The TENS apparatus of claim 9 wherein:
(a) in the first stage of the program of pulse waveforms, the waveform is applied in pulsed modulated frequencies ranging between 80 Hz and 120 Hz;
(b) in the second stage of the program of pulse waveforms, the waveform is applied in pulsed modulated frequencies ranging between 5 Hz and 10 Hz; and
(c) in the third stage of the program of pulse waveforms, the waveform is applied in pulsed modulated frequencies ranging between 80 Hz and 120 Hz.

11. The TENS apparatus of claim 9 wherein each of the pulse waveforms that are generated by the pulse driver of the portable TENS device are characterized by a positive pulse followed by a negative pulse that is of a different shape.

* * * * *